Figure 1:
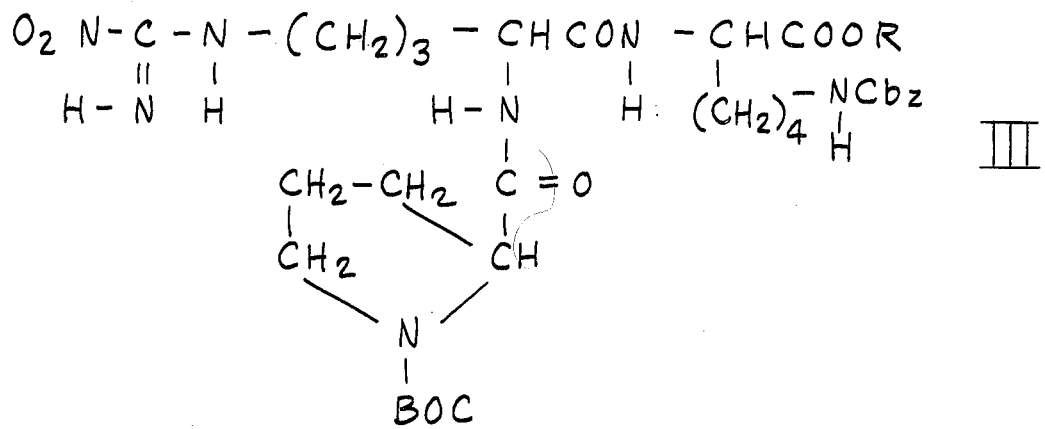
Figure 2:
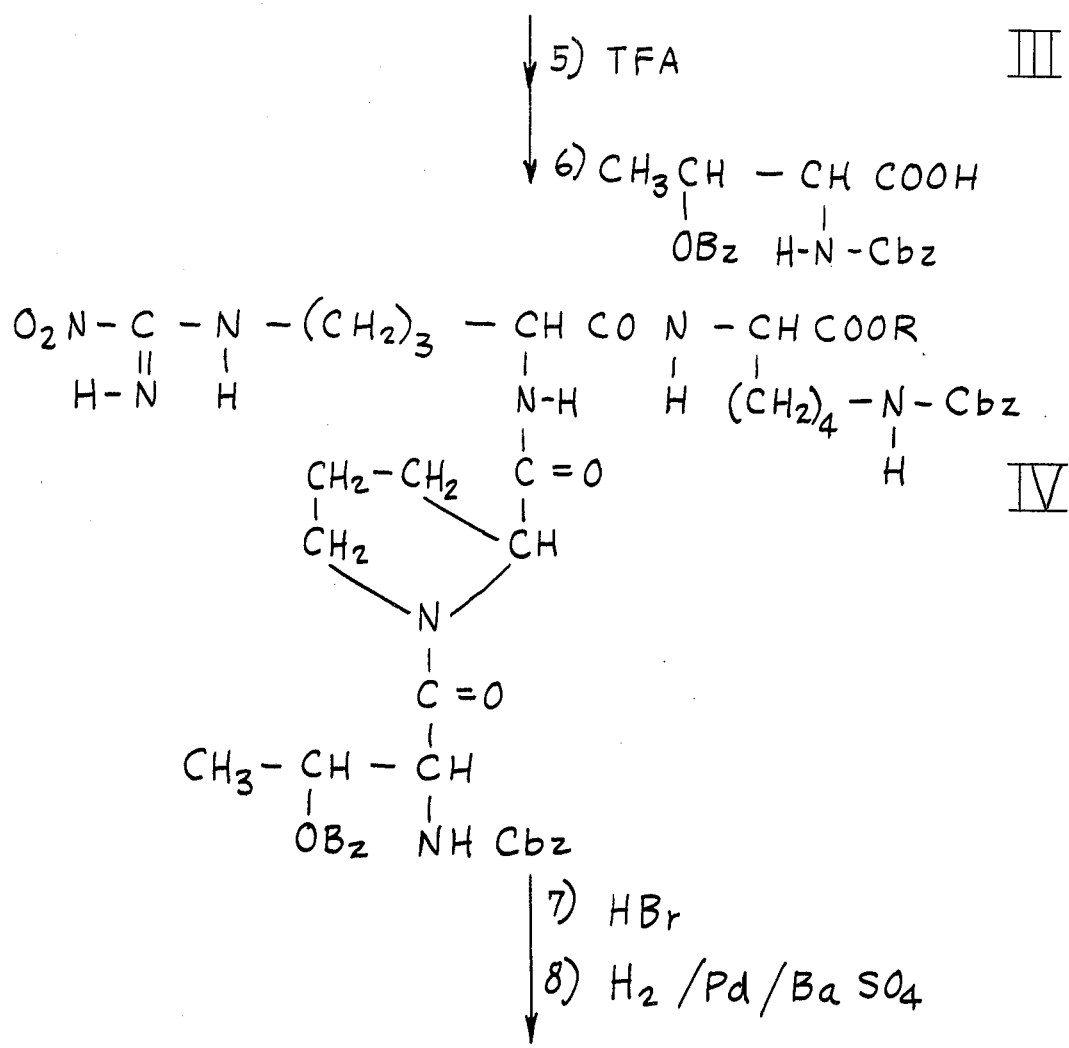
Figure 2:
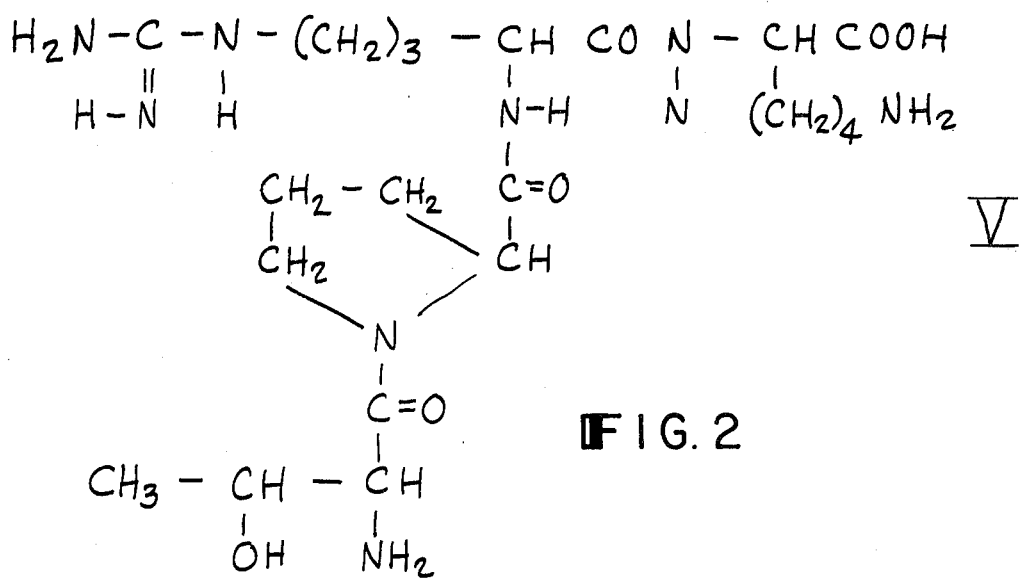

United States Patent [19]

Kent, Jr.

[11] 4,016,259

[45] Apr. 5, 1977

[54] CONTRACEPTIVE POLYPEPTIDES

[75] Inventor: Harry A. Kent, Jr., Athens, Ga.

[73] Assignee: Research Corporation, New York, N.Y.

[22] Filed: May 23, 1975

[21] Appl. No.: 580,235

Related U.S. Application Data

[63] Continuation-in-part of Ser. No. 492,179, July 26, 1974, abandoned.

[52] U.S. Cl. .......................... 424/177; 260/112.5 R
[51] Int. Cl.² ................ C07C 103/52; A61K 37/00
[58] Field of Search ............. 260/112.5 R; 424/177

[56] References Cited

UNITED STATES PATENTS

| 3,778,426 | 12/1973 | Najjar | 260/112.5 R |
| 3,884,896 | 5/1975 | Blomback et al. | 260/112.5 R |
| 3,886,136 | 5/1975 | Claeson et al. | 260/112.5 R |

*Primary Examiner*—Lewis Gotts
*Assistant Examiner*—Reginald J. Suyat
*Attorney, Agent, or Firm*—Cooper, Dunham, Clark, Griffin & Moran

[57] ABSTRACT

Polypeptides containing at least four amino acids are useful as mammalian contraceptives.

18 Claims, No Drawings

CONTRACEPTIVE POLYPEPTIDES

The invention described herein was made in the course of work under a grant or award from the Department of Health, Education and Welfare.

RELATED APPLICATION

This application is a continuation-in-part of U.S. application Ser. No. 492,179 filed July 26, 1974, now abandoned.

BACKGROUND OF INVENTION

This invention is concerned with novel polypeptides particularly polypeptides containing at least four and up to about eight amino acids as well as their pharmacologically acceptable derivatives and salts. These compounds are useful both orally and parenterally as mammalian contraceptives.

The principal class of compounds now utilized as contraceptives for animals, including humans, are steroidal in nature. The most widely employed agents are combinations of progestogens such as norethindrone and ethynodiol with estrogens such as ethynyl estradiol and mestranol. The use of such oral contraceptives is associated with a certain degree of well recognized risk. The principal risk is the occurrence of thromboembolism, although other side effects such as increased blood pressure and alterations in metabolism of both lipids and carbohydrates have been recognized, as well as a variety of other symptoms such as headache, fluid and salt retention, bloating, and nausea.

Accordingly, the art has long been interested in finding suitable substitutes for steroidal contraceptives.

THE INVENTION

A novel tetrapeptide has now been isolated from the two to four cell developmental stages in the oviducts of progravid hamsters. This tetrapeptide, and certain related peptides, derivatives and salts, when administered orally or parenterally to animals, are useful contraceptives. The product which has been isolated is threonyl-prolyl-arginyl-lysine.

For convenience, the standard abbreviations for amino acids will hereinafter be used.

| | |
|---|---|
| Thr — threonine | Ser — serine |
| Pro — proline | HyPro — hydroxy proline |
| Arg — arginine | Orn — ornithine |
| Lys — lysine | His — histidine |

Thus the above-identified tetrapeptide is designated as:

Thr-Pro-Arg-Lys

This is the basic unit upon which the invention is based. Certain modifications to be hereinafter described may be employed to form other useful compounds. However, the basic unit will always have an hydroxyl substituted amino acid as the amino terminal acid. This may be either Thr or Ser.

Modifications of the basic unit include:
1. Thr replaced with Ser to produce;
  Ser-Pro-Arg-Lys
2. Pro replaced with HyPro to produce;
  Thr-HyPro-Arg-Lys
  Ser-HyPro-Arg-Lys
3. Arg replaced with Lys to produce;
  Thr-Pro-Lys-Lys
  Ser-Pro-Lys-Lys
  Thr-HyPro-Lys-Lys
  Ser-HyPro-Lys-Lys
4. Lys replaced with Arg to produce;
  Thr-Pro-Arg-Arg
  Ser-Pro-Arg-Arg
  Thr-HyPro-Arg-Arg
  Ser-HyPro-Arg-Arg
5. Lys replaced with Arg, and Arg replaced with Lys to produce;
  Thr-Pro-Lys-Arg
  Ser-Pro-Lys-Arg
  Thr-HyPro-Lys-Arg
  Ser-HyPro-Lys-Arg
6. Arg replaced with Orn to produce;
  Thr-Pro-Orn-Lys
  Ser-Pro-Orn-Lys
  Thr-HyPro-Orn-Lys
  Ser-HyPro-Orn-Lys
  Thr-Pro-Orn-Orn
  Ser-Pro-Orn-Orn
  Thr-HyPro-Orn-Orn
  Ser-HyPro-Orn-Orn
  Thr-Pro-Lys-Orn
  Ser-Pro-Lys-Orn
  Thr-HyPro-Lys-Orn
  Ser-HyPro-Lys-Orn
7. Arg replaced with His to produce;
  Thr-Pro-His-Lys
  Ser-Pro-His-Lys
  Thr-HyPro-His-Lys
  Ser-HyPro-His-Lys
  Thr-Pro-His-His
  Ser-Pro-His-His
  Thr-HyPro-His-His
  Ser-HyPro-His-His
  Thr-Pro-Lys-His
  Ser-Pro-Lys-His
8. Lys replaced with Orn to produce:
  Thr-Pro-Arg-Orn
  Ser-Pro-Arg-Orn
  Thr-HyPro-Arg-Orn
  Ser-HyPro-Arg-Orn
  Thr-Pro-Lys-Orn
  Ser-Pro-Lys-Orn
  Thr-HyPro-Lys-Orn
  Ser-HyPro-Lys-Orn
  Thr-Pro-Orn-Arg
  Ser-Pro-Orn-Arg
  Thr-HyPro-Orn-Arg
  Ser-HyPro-Orn-Arg
9. Lys replaced with His to produce:
  Thr-Pro-Arg-His
  Ser-Pro-Arg-His
  Thr-HyPro-Arg-His
  Ser-HyPro-Arg-His
  Thr-Pro-Lys-His
  Ser-Pro-Lys-His
  Thr-HyPro-Lys-His
  Ser-HyPro-Lys-His
  Thr-Pro-His-Arg
  Ser-Pro-His-Arg
  Thr-HyPro-His-Arg
  Ser-HyPro-His-Arg 10. Lys replaced with Orn, and Arg replaced with His to produce:
Thr-Pro-His-Orn
Ser-Pro-His-Orn
Thr-HyPro-His-Orn
Ser-HyPro-His-Orn
Thr-Pro-Orn-His
Ser-Pro-Orn-His
Thr-HyPro-Orn-His 2 Ser-HyPro-Orn-His
Thr-Pro-Orn-His
Ser-Pro-Orn-His
Thr-HyPro-Orn-His
Ser-HyPro-Orn-His Useful derivatives of the above mentioned tetrapeptides can be prepared by standard, well known chemical procedures. Most of these derivatives are prepared by reactions involving active hydrogens on, for example, free hydroxyl, amino, or carboxyl groups. For example, free hydroxyl, amino or guanidino nitrogens can be acylated with acyl groups containing up to about eighteen carbon atoms. Such modifications, especially when the acyl group contains ten or more carbon atoms increases the lipid solubility of the compound and facilitates transport across cell barriers. The arginine moiety may be nitrated.

It is also useful to acylate a free hydroxyl or amino group with another amino acid. Thus the hydroxyl group on Thr, Ser or HyPro; or the guanidino group on Arg; or the epsilon amino group on Lys can be derivatized with another amino acid such as glycine, phenylalanine, lysine, etc. This procedure is especially useful when the compound is to be administered orally, since the presence of the additional amino acid helps to protect the basic unit against attack by proteolytic enzymes of the digestive system.

The carboxyl group on the carboxyl terminal of the basic unit, or the amino group on the amino terminal of the basic unit may also serve as a reaction site for the addition of amino acids to extend the basic tetrapeptide unit to form peptides containing up to about eight amino acids. The unit might be repeated by combination of the carboxyl group of the lysine terminus of one tetrapeptide with the epsilon amino group on the lysine terminus of another identical tetrapeptide.

The terminal amino group might also be combined with the carboxyl group of cysteine. Oxidation of the resulting pentapeptide forms a nonapeptide dimer linked through cystine.

Hydrophilicity may be increased by derivatizing free hydroxyl groups with saccharides, particularly monosaccharides such as glucose, galactose, mannose and the like in hemiacetal formation.

Free carboxyl groups can be stabilized by conversion to amides or esters.

The reactions employed in the formation of these various derivatives are well known.

A particular advantage arising from the amphoteric nature of the peptides of this invention is that they can be utilized in the form of pharmacologically acceptable salts. These salts have the advantage of increased water solubility and are particularly useful for parenteral administration. Of the metallic salts, the alkali and alkaline earth metal salts are preferred. The sodium salts are especially preferred because of their ease of preparation.

The acids which may be used to prepare the pharmacologically acceptable acid addition salts of this invention are those containing non-toxic anions and include, for example, hydrochloric, sulfuric phosphoric, acetic, lactic, citric, tartaric, oxalic succinic, maleic, gluconic, saccharic, and the like acids.

From an analysis of the above it will be apparent that the products of this invention can be defined as polypeptides containing at least four and up to about eight amino acids, the four amino acids being;

1. selected from the group consisting of Thr, Pro, Arg, Lys, Ser, HyPro, Orn and His, and
2. formed in a tetrapeptide unit, the amino terminus of which is Thr or Ser, said Thr or Ser being joined in a peptide bond through its carboxyl group to the amino group of Pro or HyPro;

the remaining two amino acids in said tetrapeptide being selected from the group consisting of Arg, Lys, Orn and His; and pharmacologically acceptable salts and derivatives thereof.

While it is generally preferred that the additional amino acids jointed to the basic peptide unit be selected from the eight amino acids listed above, or cysteine, it is not essential that they be so selected. Any of the known amino acids can be selected.

The preferred amino acids for all of the peptides used in this invention are the naturally occurring L-amino acids.

The most generally preferred basic unit tetrapeptides from the point of view of activity and preparative costs, are those in which the amino terminal amino acid is Thr or Ser, the next adjacent amino acid is Pro or HyPro, and the final two amino acids are Arg and Lys in that order.

The products of this invention may be administered alone but will generally be administered with pharmaceutically acceptable, non-toxic carriers, the proportions of which are determined by the suitability and chemical nature of the particular carrier, the chosen route of administration, and standard pharmaceutical practice. For example, they may be administered orally in the form of tables or capsules containing such excipients as starch, milk sugar, certain types of clay, etc. They may be enteric coated so as to be more resistant to the acid with digestive enzymes of the stomach. For intravenous and intramuscular administration they may be used in the form of a sterile solution containing other solutes, for example, enough saline or glucose to make the solution isotonic. They may be administered in an oil vehicle such as sesame oil.

The products of this invention are useful mammalian therapeutic agents. The physician or veterinarian will determine the dosage which will be most suitable. It may vary from patient to patient depending on the factors which are readily evaluated by those skilled in the art.

Dosage units containing from about 0.15 to 0.5 mg. are useful. A typical regimen for subcutaneous administration for an average sized woman is about 0.2 mg. per day. It may vary appreciably with oral administration since some of the active material may be hydrolyzed in the intestinal tract. However, as indicated above, the basic tetrapeptide unit may also be protected against premature hydrolysis by the formation of derivatives, particularly peptides containing additional amino acids.

A particular advantage of the products of this invention is that because of their relatively low molecular weight, there is no danger of an immune response.

The tetrapeptide of this invention exists in the hamster source, and probably in other species as a part of a larger molecule. This large molecule is not itself therapeutically useful. One reason for this, among many others, is that it triggers an antigen antibody response in the host. Another is that it is too difficult to isolate in useful quantities. The tetrapeptide, on the other hand, can be readily synthesized chemically in useful therapeutic quantities at reasonable cost.

The isolation procedure for the tetrapeptide of this invention is as follows:

The oviducts were removed from 10 progravid hamsters at 40 hours postcoitum. The oviducts were opened with a microknife at the ampullary area. It was possible to see the two-cell stages with direct and indirect lighting using a 70 power dissecting scope. The cells were collected with an eyedropper from added ion free water, centrifuged at 300 G. and the supernatent discarded. The residue was washed in 0.02 M ammonium acetate, and then washed into a Teflon and glass homogenizer, homogenized and thereafter lyophilized from a lyophilizing tube.

The residue was reconstituted with 0.02 M ammonium acetate and put on a 0.9 × 71 cm G-10 Sephadex column (3 washes with a total volume of 1 ml.). The column was eluted with 0.02 M ammonium acetate. 1 ml. aliquots were collected and the broad areas rerun. Successive reruns gave isolation of 4 peaks at 260 to 280 nm; I, IA, II and III. Peak I appeared immediately after the void volume and was followed by a very small IA peak.

The IA fraction is the active fraction. This was determined by injection into 3 animals at 0.1 ml/day for 4 days beginning on the morning after the third consecutive heat. The ovaries were removed on day 5 and analyzed for corpora lutea and mature graffian follicules. With the biologically active fraction none were found.

Fraction IA was analyzed for amino acid content on the Beckman/Spince 20 amino acid analyzer machine using both acid and basic columns. It was found that the amino acids present were Thr, Pro, Lys and Arg. Edman Degradation with dansylation of the exposed N-terminal groups was utilized to establish the amino acid sequence.

The peptides of this invention can be synthesized by any of a wide variety of techniques now available for the synthesis of simple and complex polypeptides and even relatively low molecular weight proteins. In general, these techniques involve stepwise synthesis by successive additions of amino acids to produce progressively larger molecules. The amino acids are linked together by condensation between the carboxyl group of one amino acid and the amino group of another amino acid to form a peptide bond. In order to control these reactions it is necessary to block the amino group of the one acid and the carboxyl group of the other. Necessarily, the blocking groups must be easily removed. The whole series of reactions must take place without causing racemization of the products.

A large number of procedures have been devised by the art for the synthesis of polypeptides and a wide variety of blocking agents are known. Most of these procedures are applicable to the synthesis of the polypeptides of this invention. No useful purpose would be served by describing the application of all of them.

Two of the procedures which may be used are the Merrifield technique and the N-carboxy anhydride technique. In the former an amino acid is first bound to a resin particle, as by an ester bond and the peptide is generated in a stepwise manner by successive additions of protected amino acids to the growing chain. In the latter, an N-carboxyl amino acid anhydride is reacted with the amino group of a second amino acid or peptide under conditions such that the only amino group present in appreciable concentration in reactive form during the course of the reaction is the amino group which is to participate in the reaction. This control is effected by selection of concentration, temperature, time and hydrogen ion concentration. The coupling reaction normally takes place under alkaline conditions, usually at a pH of from about 8.5 to 11. The intermediate carbamate is then decarboxylated by lowering the pH to from about 3 to 5. The product formed may be reacted with another N-carboxy amino acid anhydride without isolation and under substantially the same conditions. The process affords a very rapid method for the production of polypeptides.

Salts of the peptides are prepared by conventional procedures, for example by titration with aqueous acid or base.

The synthesis illustrated in the Appendix shows one of the many methods that are available to synthesize the basic unit tetrapeptide of this invention. In the equations the standard abbreviations normally employed in this art are utilized. Thus:

BOC is t-butoxy
DC is dicyclohexylcarbodiimide
Cbz is carbobenzoxy
TFA is trifluoro acetic acid
R is the resin
Bz is benzyl The synthesis illustrated is applicable to the preparation of all of the tetrapeptides listed above. While the synthesis shows the use of Lys, Arg, Pro and Thr, it is also applicable to the preparation of tetrapeptides containing HyPro, Ser, Orn and His. The hydroxyl group on HyPro and the imino group in His do not need to be protected. However, it is convenient, and perhaps better to protect the hydroxyl with a Bz group and the amino with a Cbz group. Both protecting groups can be removed by catalytic hydrogenation. Orn is similar to Lys and can be treated in substantially the same manner. Ser is similar to Thr and can also be treated in exactly the same manner.

Example 1 shows the process as applied to the preparation of a number of illustrative tetrapeptides of the invention. It should be understood, however, that the process is illustrative and not limiting since, as indicated above, any of a large number of known peptide syntheses are applicable to the preparation of the compounds of this invention.

For the preparation of peptides containing more than four amino acids the illustrated process is easily utilized at either end of the tetrapeptide. For example, the amino acid linked to the resin could be leucine. The product produced would then be:

Thr-Pro-Arg-Lys-Leu

Alternatively the chain could be lengthened from the amino terminal by the addition of an amino acid such as alanine or even a peptide such as Lys-Arg.

The contraceptide compounds of this invention are useful in mammalian species to control the development of pregnancies.

In one study carried out with hamsters Thr-Pro-Arg-Lys as the diacetate was administered subcutaneously in isotonic solution at dosage levels of 2, 10 and 100 micrograms per gram of body weight per day, once daily starting on the day of postovulatory discharge (−4) prior to mating. Treatment was continued until the fourth day after ovulation. The animals were mated and then sacrificed on the tenth day. The uterus was opened, and the number of implants counted. The results are shown in Table I.

TABLE I

| TEST Female Anti-Fertility | SPECIES Hamster | | | | | |
|---|---|---|---|---|---|---|
| DAY OF SPERM = DAY 0 | VEHICLE Saline | ROUTE OF ADMINISTRATION Subc. | | | | |
| DAY OF AUTOPSY Day - 10 | TREATMENT SCHEDULE | Once daily for four days, starting on the day of postovulatory discharge, prior to mating. | | | | |
| Daily Dose $\mu g/100$ mg | Duration of Treatment (day) | Total No. of Animals Sperm + | No. of Animals with Implantations | Total No. of Normal Fetuses | Total No. of Resorbing Fetuses | Average No. of Implants |
| 2.0 | (−4)–(−1) | 10/10 | 9 | 82 | 2 | 9.1 |
| 10.0 | " | 10/10 | 1 | 5 | 0 | 0.5 |
| 100.0 | " | 10/10 | 4 | 46 | 3 | 4.6 |
|  | " | 9/10* | 4 | 53 | 1 | 5.9 |

*One hamster: no sperm found, 5 eggs recovered

In still another test hamsters were treated subcutaneously in the same manner with defined quantities of the same compound in phosphate buffer at pH 7.1. Calculated as the free base the quantities administered were ranged from about 0.35 to 70 $\mu g/100$ g/day. The control of pregnancy was determined by removing the ovaries after 10 days and histologically counting the number of corpora lutea with a diameter of at least 0.4 mm. It was found that the number of implantations per animal could be reduced to less than one at an effective dose of 0.7 mcg/gm/day. When administered orally at 35 to 50 $\mu g/100$ gm/day, the number of pregnancies was reduced to zero.

The following examples are given by way of illustration only.

EXAMPLE I

Thr-Pro-Arg-Lys

N$^\epsilon$-Cbz-Lys, 13.8 mmoles are reacted with 10 g. of chloromethyl-resin (polystyrene divinyl benzene chloromethyl resin 2.2 mmoles of chloride per gram of resin) in a mixture of triethylamine, 12.4 mmoles, and 30 ml. ethanol for 24 hours at 80° C. with constant magnetic stirring. The resin is then thoroughly washed with acetic acid, then with absolute ethanol, water with increasing concentration of ethanol, finally with absolute ethanol followed by methanol and methylene chloride. The resin is dried in vacuo to constant weight.

1.5 g. of resin representing 0.45 mmoles of N$^\epsilon$-Cbz-Lys are placed in the Merrifield solid phase vessel secured onto a clamp to the shafe of a 180° reversible stroke motor. All manipulations henceforth take place at room temperature with 180° rocking motion such that the resin is constantly agitated. The protecting t-BOC group is cleaved with 15 ml. of 50% of TFA in methylene chloride for a 30 minute reaction time. The resin is then washed with methylene chloride followed by chloroform 3× each with 15 ml. 1 ml. triethylamine plus 9 ml. of chloroform was added to the resin and shaken for 10 minutes to neutralize the hydrochloride. This is washed again with chloroform and methylene chloride as before. t-BOC-N$^g$-nitro-Arg 1.35 mmoles in 15 ml of methylene chloride is then coupled to the N$^a$ of Lys with 1.35 mmoles of DCC for two hours with continuous shaking. The resin is washed with ethanol, chloroform and methylene chloride, 15 ml. of each 3 times, respectively. The t-BOC group is removed from the Lys with 50% trifluoroacetic acid in methylene chloride, washed and neutralized with triethylamine as before. In a similar manner, t-BOC-Pro 1.35 mmoles is coupled to Arg, deprotected, neutralized and 1.35 mmoles of N$^a$-t-BOC-O-benzyl threonine is then coupled to the deprotected N$^a$ of Pro. Thus the steps of deprotection (cleavage of the t-BOC alone) with TFA, washing, neutralization with triethylamine, washing and coupling with DCC is repeated for each amino acid residue in an identical manner.

30 mg. of the tetrapeptide resin are hydrolyzed with 6 N hydrochloric acid in dioxane for 18 hours and the product assayed on the amino acid analyzer. It yields a ratio of Thr 1, Lys 1, Pro 1, Arg 1. The value for Arg is the sum of Arg, Orn and nitro Arg. The tetrapeptide is cleaved off the resin with hydrogen bromide in TFA at room temperature for 1- ½ hours. It is then dried in vacuo, washed twice with water and lyophilized. Its weight of 176 mg. represents a 78% yield based on Lys. It is then taken up in 10 ml. of methanol containing 10% acetic acid. This is then exposed to catalytic hydrogenation with twice its weight 350 mg. of palladium on barium sulfate in a hydrogen atmosphere at 60 pounds per square inch pressure with continuous shaking for 24 hours at which time no nitro Arg is detected at 271 m$\mu$, the peak of absorption. An aliquot is again hydrolyzed with 6 N HCl in water and assayed. This yields a comparable figure for Thr, Lys, Pro, and Arg.

The tetrapeptide which is in the form of the diacetate salt is then converted to the sodium salt by the addition of three equivalents of sodium hydroxide.

The final yield is about 65%.

The process is repeated to form the tetrapeptide with all amino acids in the D-form. It is repeated twice with Ser in place of Thr. Both all L-and all D-forms are prepared.

The following compounds are similarly prepared.
Thr-HyPro-Arg-Lys
Ser-HyPro-Arg-Lys
Ser-Pro-Lys-Lys
Ser-HyPro-Lys-Lys
Ser-Pro-Arg-Arg
Ser-HyPro-Arg-Arg
Thr-Pro-Lys-Arg
Ser-Pro-Lys-Arg
Ser-HyPro-Lys-Arg
Ser-Pro-Orn-Lys
Ser-HyPro-Orn-Lys
Ser-Pro-Orn-Orn Thr-Pro-Lys-Orn
Ser-HyPro-Lys-Orn
Ser-HyPro-His-Lys
Thr-Pro-Lys-His
Thr-Pro-Arg-Orn
Ser-Pro-Arg-Orn
Thr-Pro-Lys-Orn
Thr-Pro-Arg-His
Thr-HyPro-Arg-His
Thr-Pro-Lys-His
Ser-Pro-Lys-His
Thr-Pro-His-Orn
Thr-HyPro-His-Orn

EXAMPLE II

STEARYL-Thr-Pro-Arg-Lys 0.45 mmole of O-Bz-Thr-Cbz-Pro-$N^\alpha$-NitroArg-$N^\epsilon$-Lys resin ester on 1.3 g. of resin is coupled to 1.5 mmoles of stearic acid using dicyclohexylcarbodiimide 1.5 mmoles, in 1:1 chloroform:dimethylformamide. The remainder of the procedure for cleavage from the resin with HBr in $CF_3COOH$ (TFA), deprotecting Thr and Lys and catalytic hydrogenation of the NitroArg to Arg and ammonia is as in the previous example. The final yield is 63%–71%. Similar results are obtained with the other fatty acids with a yield varying from 37 to 67%. This includes acetic, propionic, butyric, lauric, myristic, palmitic, oleic, linoleic, and linolinic. In the case of the last three which are unsaturated, fatty acids hydrogenation cannot be used since this would reduce the olefinic unsaturation. Instead the peptide resin is treated with hydrogen fluoride under anhydrous conditions to remove all protecting groups. The yield with the unsaturated fatty acids for the final products is at the lower ranges, 48 –55%.

APPENDIX

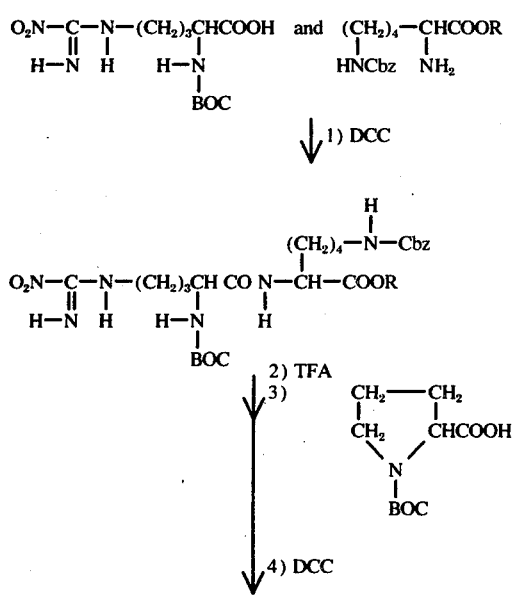

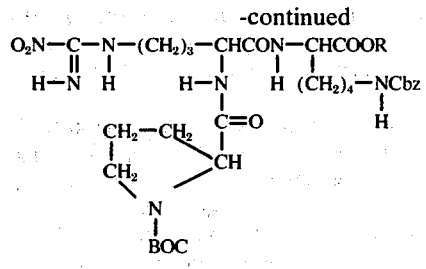

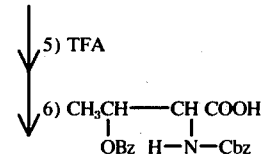

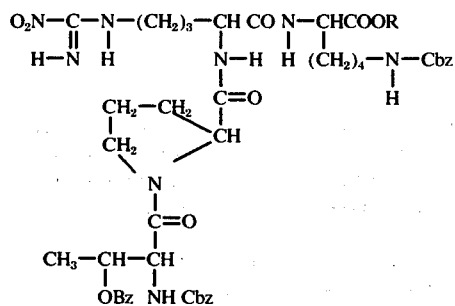

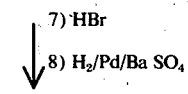

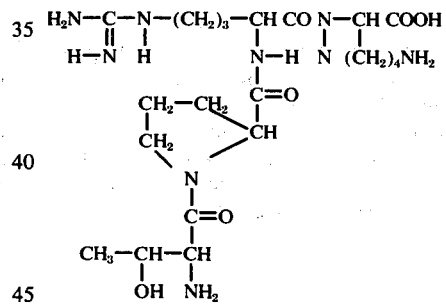

What is claimed is:
1. Polypeptides containing at least four, and up to about eight, amino acids, the four amino acids being:
   1. selected from the group consisting of threonine, proline, arginine, lysine, serine, hydroxyproline, ornithine and histidine; and
   2. formed in a tetrapeptide unit, the amino terminus of which is the amino acid threonine or serine, said threonine or serine being formed in a peptide bond through its carboxyl group to the amino group of proline or hydroxyproline;
   the remaining two amino acids in said tetrapeptide unit being selected from the group consisting of arginine, lysine, ornithine and histidine,
   and pharmacologically acceptable salts thereof.
2. Polypeptides of claim 1 containing four amino acids in which the amino terminus is threonine or serine and pharmacologically acceptable salts thereof.
3. Polypeptides of claim 2 wherein the amino terminus is threonine or serine and joined in a peptide bond through its carboxyl group to the amino group of pro- line or hydroxyproline and the remaining two amino acids are selected from the group consisting of arginine and lysine and pharmacologically acceptable salts thereof.

4. Polypeptides of claim 3 wherein the sequence of the said remaining two acids is arginine joined through its carboxyl group to the alpha amino group of lysine and pharmacologically acceptable salts thereof.

5. Polypeptides of claim 3 wherein sequence of the said remaining two acids is lysine joined through its carboxyl group to the amino group of arginine and the pharmacologically acceptable salts thereof.

6. Thr-Pro-Arg-Lys and pharmacologically acceptable salts thereof.

7. Thr-Pro-Lys-Arg and pharmacologically acceptable salts thereof.

8. Thr-HyPro-Arg-Lys and pharmacologically acceptable salts thereof.

9. Thr-HyPro-Lys-Arg and pharmacologically acceptable salts thereof.

10. A composition comprising a pharmaceutically acceptable carrier and at least one compound selected from the group consisting of polypeptides containing at least four, and up to about eight, amino acids, the four amino acids being:
  1. selected from the group consisting of threonine, proline, arginine, lysine serine, hydroxyproline, ornithine and histidine; and
  2. formed in a tetrapeptide unit, the amino terminus of which is the amino acid threonine or serine, said threonine or serine being formed in a peptide bond through its carboxyl group to the amino group of proline or hydroxyproline;
  the remaining two amino acids in said tetrapeptide unit being selected from the group consisting of arginine, lysine, ornithine and histidine,
  and pharmacologically acceptable salts thereof.

11. A composition comprising a pharmaceutically acceptable carrier and at least one compound selected from the group consisting of polypeptides of claim 10 containing four amino acids in which the amino terminus is threonine or serine and pharmacologically acceptable salts thereof.

12. A composition comprising a pharmaceutically acceptable carrier and at least one compound selected from the group consisting of polypeptides of claim 11 wherein the amino terminus is threonine or serine and joined in a peptide bond through its carboxyl group to the amino group of proline or hydroxyproline and the remaining two amino acids are selected from the group consisting of arginine and lysine and pharmacologically acceptable salts thereof.

13. A composition comprising a pharmaceutically acceptable carrier and at least one compound selected from the group consisting of polypeptides of claim 12 wherein the sequence of the said remaining two acids is arginine joined through its carboxyl group to the alpha amino group of lysine and pharmacologically acceptable salts thereof.

14. A composition comprising a pharmaceutically acceptable carrier and at least one compound selected from the group consisting of polypeptides of claim 12 wherein sequence of said remaining two acids is lysine joined through its carboxyl group to the amino group of arginine and the phamacologically acceptable salts thereof.

15. A composition comprising a pharmaceutically acceptable carrier together with a compound selected from the group consisting of Thr-Pro-Arg-Lys and pharmacologically acceptable salts thereof.

16. A composition comprising a pharmaceutically acceptable carrier together with a compound selected from the group consisting of Thr-Pro-Lys-Arg and pharmacologically acceptable salts thereof.

17. A composition comprising a pharmaceutically acceptable carrier together with a compound selected from the group consisting of Thr-HyPro-Arg-Lys and pharmacologically acceptable salts thereof.

18. A composition comprising a pharmaceutically acceptable carrier together with a compound selected from the group consisting of Thr-HyPro-Lys-Arg and pharmacologically acceptable salts thereof.

* * * * *